(12) United States Patent
Spiering

(10) Patent No.: US 6,318,651 B1
(45) Date of Patent: Nov. 20, 2001

(54) MILL, IN PARTICULAR FOR MILLING OF BONE, AS WELL AS A DRUM, PROVIDED WITH CUTTING MEMBERS, APPLICABLE IN THE MILL

(76) Inventor: Petrus Tarasius Josephus Spiering, Madoerastraat, 24, 6524 LH Nigmegen (NL)

(*) Notice: Subject to any disclaimer, the term of this patent is extended or adjusted under 35 U.S.C. 154(b) by 0 days.

(21) Appl. No.: 09/367,135
(22) PCT Filed: Feb. 10, 1998
(86) PCT No.: PCT/NL98/00081
§ 371 Date: Aug. 6, 1999
§ 102(e) Date: Aug. 6, 1999
(87) PCT Pub. No.: WO98/34491
PCT Pub. Date: Aug. 13, 1998

(30) Foreign Application Priority Data

Feb. 11, 1997 (NL) .................................................... 1005251

(51) Int. Cl.$^7$ .................................................... B02C 18/18
(52) U.S. Cl. .............................................. 241/93; 241/293
(58) Field of Search ........................................ 241/93, 293

(56) References Cited

U.S. PATENT DOCUMENTS 2,228,025 * 1/1941 Apfelbeck ............................. 241/93
4,061,280 * 12/1977 Box .

FOREIGN PATENT DOCUMENTS

1094782 * 5/1955 (FR) .
9402781-0 2/1999 (SE) .

* cited by examiner

Primary Examiner—Mark Rosenbaum
(74) Attorney, Agent, or Firm—Milde, Hoffberg & Macklin, LLP

(57) ABSTRACT

A mill comprises a housing (3) and a drum (15), provided with cutting members (17), which is rotatably located inside the housing. The cutting members and the drum are made from one piece and the cutting members are formed by local thickenings of the wall of the drum. The cutting members have a cutting edge from which one point (41) protrudes in the circumferential direction of the drum, such that during operation the cutting members contact the material to be milled with this point first. The cutting members are located on the intersection of an imaginary spiraled line (47) around the drum and a number of imaginary oblique lines (49), which run at an angle with the axial direction of the drum. The cutting members are formed by machining the outer surface of a thick-walled drum, such that on the outer surface of that drum a spiral-shaped rim remains, which is removed at a number of places. Cutting edges with clearance surfaces are machined at the remaining parts of the rim.

15 Claims, 3 Drawing Sheets

MILL, IN PARTICULAR FOR MILLING OF BONE, AS WELL AS A DRUM, PROVIDED WITH CUTTING MEMBERS, APPLICABLE IN THE MILL

FIELD OF THE INVENTION

The invention relates to a mill, in particular for milling of bone, comprising a housing provided with at least one opening, for supply of material to be milled an removal of machined chips, and a drum, provided with cutting members, which is rotably located inside the housing. With milling is meant the whole of manufacturing methods of which chips can be made, such as machining, cutting, chipping, morselizing, breaking, chopping. With chips all kind of small particles are meant like e.g. splinters, flakes, pieces, slices. With cutting members all kind of tools, such as for example knives, chisels and teeth are meant, which can be used to mill a material.

The milling of bone is a known method in the medical field, where bone chips are used for the filling of defects in bones, which are created by the removal of a tumor or cyst, or are used for filling a gap between a prosthetic stem or cup and the surrounding bone of a patient in case of a revision operation, where inevitably part of the original bone stock has been lost. Further more bone chips are used among others for the correction of deviant bony structures, so called bone plastics, for the correction of fracture defects and for fusion of joints and vertebrae. Bone chips are not rejected by the human body and they integrate with the natural existing bone.

BACKGROUND OF THE INVENTION

A mill of the type mentioned at the beginning is disclosed in the Swedish patent number 9402781-0. The bone mill described inhere has a drum provided with a number of axially elongated grooves, in which cutting blocks are seated which are removably attached to the drum and all grooves are extended in one straight line parallel to the axially direction. The separate manufacturing of the drum and the cutting blocks is an expensive method of manufacturing. Because the cutting blocks are located in one straight line and because all cutting edges of one cutting block are located in one straight line, all cutting members of one cutting block come simultaneously into contact with the bone to be milled. This results in a jerkily action and an inefficient milling process.

A similar prementioned mill is also generally known, at least in the medical field, as a mill with a drum provided with round openings which are formed by bending parts of the wall of the drum outwards and grinding cutting edges on them. Due to the shape of the cutting edges, a larger force to produce the desired large size of chips is needed than with the aforementioned known bone mill. For these reasons the milling process takes more time and effort than with the aforementioned known bone mill.

SUMMARY OF THE INVENTION

An object of the invention is to provide a mill which is less expensive to manufacture than the known bone mills. Therefore the mill of the present invention is characterized in that the drum and the cutting members are made from one piece and the cutting members are formed by local thickenings of the wall of the drum. By manufacturing the drum and the number of manufacturing steps can be reduced by simultaneous manufacturing of the drum and the cutting members.

A preferred embodiment of the mill according to this invention is characterized in that the cutting members are provided with a cutting edge which with one point protrudes in the circumferential direction of the drum, such that during operation the cutting members will contact with this point first the material to be milled. As the cutting members do not contact the bone at their full width less force is needed and the force increases more gradually which makes the mill work more efficiently than the known bone mill.

This design feature can also be applied seperately without that the drum and cutting members are made from one piece and the cutting members are formed by local thickenings of the wall of the drum. For example by attaching seperate cutting members to the drum.

In order to operate at a large axial length a further embodiment is characterized in that at least part of the cutting members are mutually displaced in the axial direction of the drum.

One embodiment which can be efficiently manufactured is characterized in that at least part of the cutting members are located along an imaginary spiralled line around the drum. Such a configuration can relativily easily be realized on a lathe.

To achieve a still greater efficiency and a smoother action of the cutting members on the bone a further embodiment is characterized in that at least part of the cutting members are mutually displaced in the circumferential direction of the drum. Because of this, only one or a few cutting members contact the bone at the same moment. It is noted that also this design feature can be applied seperately without that the drum and cutting members are made from one piece and the cutting members are formed by local thickenings of the wall of the drum and also without that the cutting members protrude with one point in the circumferential direction.

A practical advantageous embodiment is characterized in that at least part of the cutting members are located along a number of imaginary oblique lines which run at an angle with the axial direction of the drum.

A practical embodiment at which both aforementioned configurations can be manufactured efficiently is characterized in that at least part of the cutting members are located at the intersections of the imaginary oblique lines and the imaginary spiralled line. In order to remove the chips a further embodiment is characterized in that aside the imaginary oblique lines, in front of the cutting members as viewed in the direction of rotation elongated slots are present.

A preferred embodiment of the mill according to the invention which can practically advantageous be manufactured is characterized in that the drum with the cutting members is formed by machining the outer surface of a thick-walled drum, such that on the outer surface of that drum a spiralshaped rim remains which is removed at a number of places and at the remaining parts cutting edges and clearance surfaces are machined.

The invention also relates to a drum provided with cutting members applicable in the mill according to the invention. Drums with cutting members can also be marketed seperately and are of course exchangeable. Therefore various drums with different numbers and sizes of cutting members can go with one housing to produce bone chips of various sizes.

BRIEF DESCRIPTION OF THE DRAWINGS

The invention will be explained in more detail hereunder by means of the drawings of an embodiment of the mill. Hereby shows.

DETAILED DESCRIPTION OF THE DRAWINGS

Figure 1:
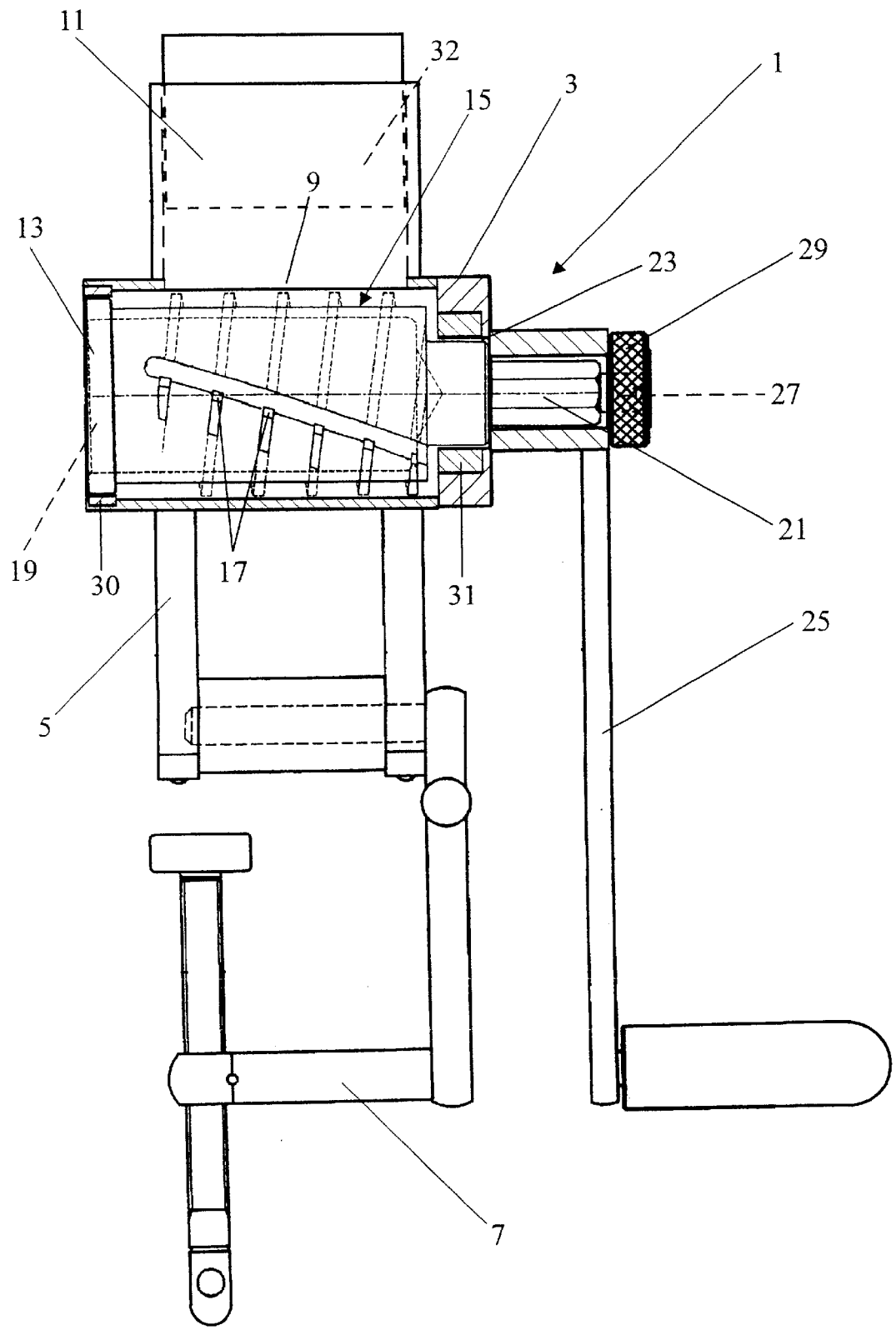
FIG. 1 a view of the mill according to the invention.

In FIG. 1 a mill according to the invention is shown. The mill 1 has a cylindrical housing 3 which can by means of a footh 5 be placed on for example a table. The mill 1 can be fastened to the table by a fastening clamp 7 which is attached to footh 5. At the upper end a supply opening 9 is located in housing 3 for the supply of bone to be milled. In order to facilitate the supply of bone a funnel 11 is located on the housing 3.

The cylindrical housing 3 is open at one end. This opening 13 serves for the introduction of a drum 15 with cutting members 17 in the housing 3. This drum 15 is also provided with an opening 19 at one end for the removal of machined chips. At the other end of drum 15 a hexagonal shaft 21 is located, which is pushed through another opening 23 located in the housing 3, and to which a handle 25 is attached. At the end of the hexagonal shaft 21 is a threaded end 27 on which a nut 29 is screwed in order to lock handle 25 on the hexagonal shaft 21. The drum 15 is supported by two bearing bushes 30 and 31 in housing 3. Inside the funnel 11 a push block 32 is located. This push block 32 is formed by a piece of metal which is placed on top of the bone in tunnel 11 and with which the bone can be pushed downwards.

The drum 15 can easily be taken out of housing 3 by unscrewing nut 29 and can then be exchanged for another drum with for example less but larger cutting members. This is in particular handy if various sizes of bone chips are needed.

Figure 2:
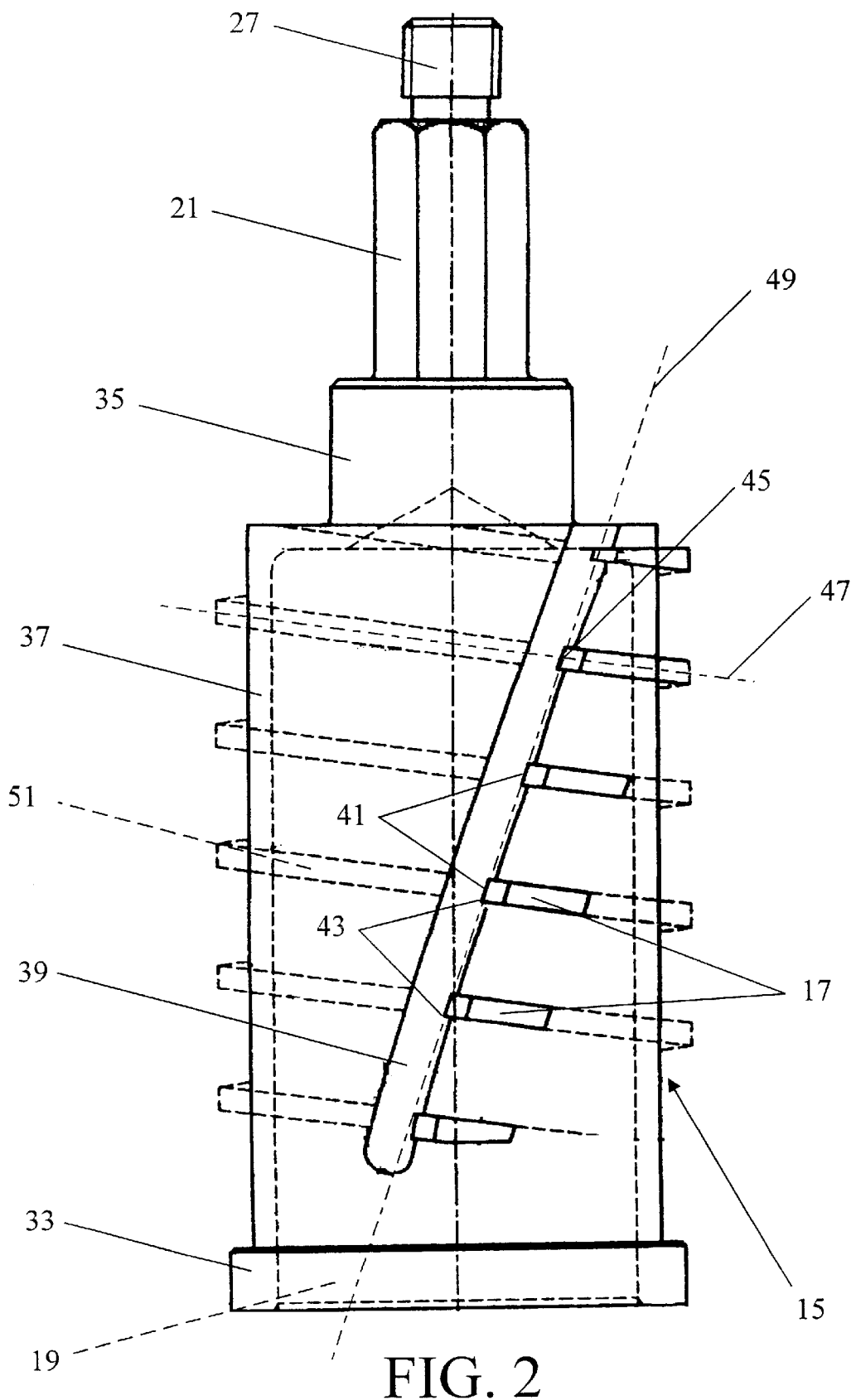
FIG. 2 a drum with cutting members according to the invention.

In FIG. 2 the drum 15 is shown alone. At one end the drum is provided with the said opening 19 and at the other end the hexagonal shaft 21 with threaded end 27 is located. At both ends the drum 15 is provided with bearing surfaces 33 and 35 which coincide with the bearing bushes 30 and 31 in the housing 3. On the drum 15 the cutting members 17 are located. The drum 15 and the cutting members 17 are made from one piece at which the cutting members 17 are formed by local thickenings of the wall 37 of the drum. Further elongated slots 39 are located in the wall 37 of the drum, in front of the cutting members 17 as viewed in the direction of rotation, through which bone chips can pass during operation.

The cutting members 17 are provided with a cutting edge 41 which with one point 43 protrude in the circumferential direction of the drum, such that during operation the cutting members 17 are located at the intersections 45 of an imaginary spiralled line 47 around the drum and a number imaginary oblique lines 49, which run at an angle with the axial direction of the drum. Thereby the cutting members 17 are mutually displaced in the axial and the circumferential direction of the drum. The pitch angle of the imaginary spiralled line 47, the number of rows of the cutting members 17 and the width of the cutting members are adjusted such that during one revolution of the drum 15 over the full axial length of the supply opening 19 at least one cutting member 17 has passed, such that the bones to be milled in the supply opening have one continuous layer of bone removed.

Figure 3:
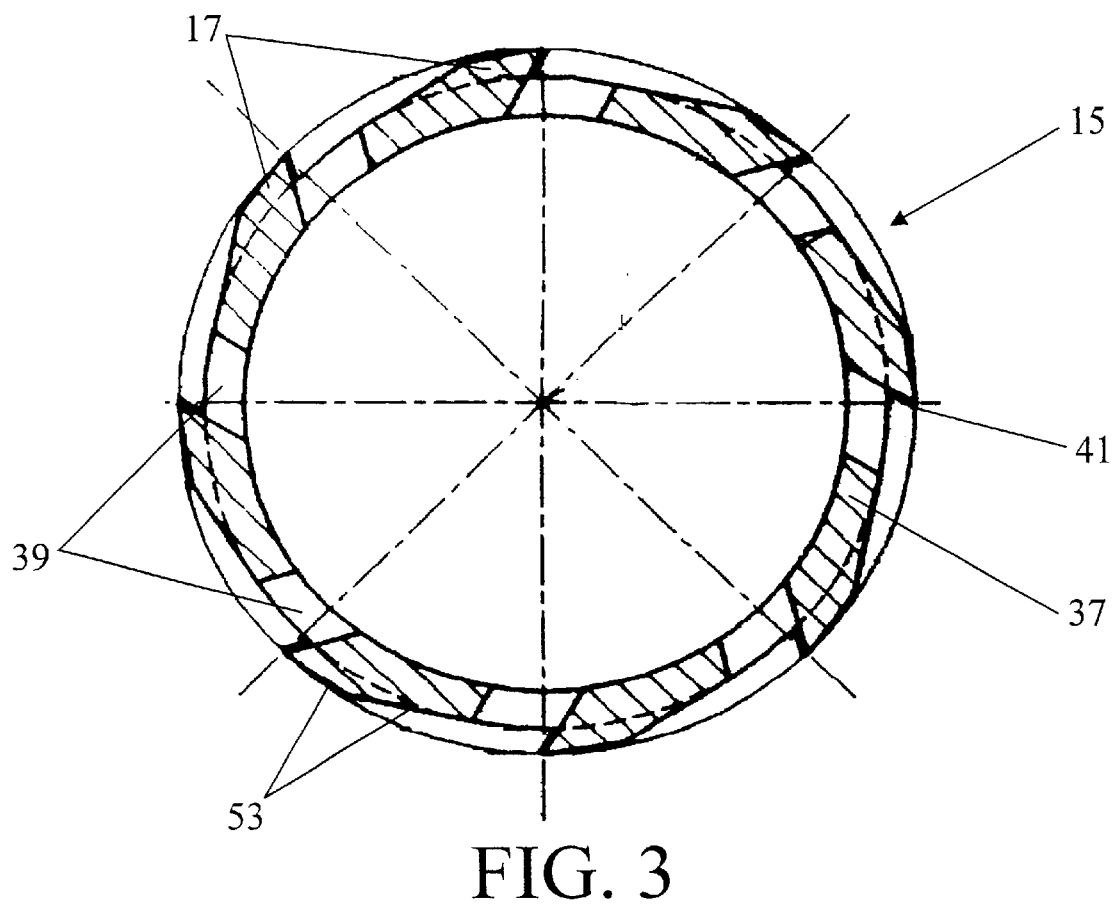
FIG. 3 a cross-section along a spiralled line of the drum.

The drum 15 and the cutting members 17 are formed by machining the outer surface of a thick-walled drum, such that on the outer surface of that drum 17 a spiralshaped rim 51 remains (shown with dotted lines) which is then removed at a number of places. At the remaining parts cutting edges 41 and clearance surfaces 53 (see FIG. 3) are machined which form the cutting members. If required these can be hardened. By way of illustration FIG. 3 shows a cross-section of drum 15 along an imaginary spiralled line 47. For easy reference only one row of cutting members is shown in FIG. 2. In reality more cutting members would been shown.

Although in the foregoing the invention has been illustrated with reference to the drawings, it must be stated that the invention is in no way limited to the embodiment shown in the drawings. The invention extends to all from the drawings deviating embodiments within the scope of the claims.

Among others it is feasible to modify the shape, location and number of cutting members. Also the exterior of the mill can be designed differently, for example by using an electric or pneumatic motor in stead of a hand driven handle or by situating the opening for removal of chips in the bottom of the housing. The manufacturing of the drum with cutting members can also be accomplished in another fashion, like for example casting followed by finishing of the cutting edges. The cutting members can, instead of along one spiralled line, be located along several spiralled lines. It also must be noted that the mill is not only suitable for milling of bone but can also be used for milling of other materials such as wood and plastics.

There has thus been shown and described a novel mill, in particular for milling of bone, which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a mill comprising a housing, having at least one opening for supply of material to be milled and for removal of machined chips, and a hollow drum, having a substantially cylindrical wall provided with a plurality of cutting members and openings therein adjacent at least some of the cutting members so that milled material can pass through the drum to its interior, which drum is rotatably located inside the housing, the improvement wherein the cutting members and the drum are made from one piece, and wherein at least some of the cutting members are disposed at a plurality of locations which are mutually displaced in the axial direction of the drum, and are formed by local thickenings of the wall of the drum.

2. Mill according to claim 1, wherein the cutting members are provided with a cutting edge which protrudes with one point in the circumferential direction of the drum, such that during operation the cutting members contact the material to be milled with this point first.

3. Mill according to claim 1, wherein at least some of the cutting members are located along an imaginary spiraled line around the drum.

4. Mill according to claim 3, wherein at least some of the cutting members are located at intersections of imaginary oblique straight lines, which extend at an angle with respect to the axis of the drum, with the imaginary spiraled line.

5. Mill according to claim 1, wherein at least some of the cutting members are mutually displaced in the circumferential direction of the drum.

6. Mill according to claim 1, wherein at least some of the cutting members are located along a number of imaginary oblique lines, which run at an angle with the axial direction of the drum.

7. Mill according to claim 6, wherein said openings are elongated slots disposed adjacent the imaginary oblique lines, in front of said some cutting members as viewed in the direction of rotation.

8. Mill according to claim 1, wherein the drum with the cutting members is formed by machining the outer surface of a thick-walled drum, such that on the outer surface of that drum a spiral-shaped rim remains, which is removed at a number of places, and wherein cutting edges and clearance surfaces are machined at the remaining parts of the rim.

9. In a hollow, substantially cylindrical drum, suitable for use in a mill, said drum having a plurality of cutting members and openings therein adjacent at least some of the cutting members so that milled material can pass through the drum to its interior, the improvement wherein at least some of the cutting members are mutually displaced in the axial direction of the drum, and wherein the cutting members and the drum are made from one piece and the cutting members are formed by local thickenings of the wall of the drum.

10. Drum according to claim 9, wherein at least some of the cutting members are located along an imaginary spiraled line around the drum.

11. Drum according to claim 9, wherein at least some of the cutting members are mutually displaced in the circumferential direction of the drum.

12. Drum according to claim 11, wherein at least some of the cutting members are located along a number of imaginary oblique lines, which run at an angle with the axial direction of the drum.

13. Drum according to claim 12, wherein said openings are elongated slots disposed adjacent the imaginary oblique lines, in front of the cutting member as viewed in the direction of rotation.

14. Drum according to claim 9, wherein at least some of the cutting members are located at the intersections of the imaginary oblique lines with the imaginary spiraled line.

15. Drum according to claim 9, wherein said drum with the cutting members and openings is formed by machining the outer surface of a thick-walled drum, such that on the outer surface of that drum a spiral-shaped rim remains, which is removed at a number of places, and wherein cutting edges and clearance surfaces are machined at the remaining parts of the rim.

* * * * *

UNITED STATES PATENT AND TRADEMARK OFFICE
CERTIFICATE OF CORRECTION

PATENT NO. : 6,318,651 B1
DATED : November 20, 2001
INVENTOR(S) : Petrus Tarasius Josephus Spierings It is certified that error appears in the above-identified patent and that said Letters Patent is hereby corrected as shown below:

<u>Title page,</u>
Item [76] Inventor: Petrus Tarasius Josephus Spierings

Signed and Sealed this

Nineteenth Day of March, 2002

Attest:

JAMES E. ROGAN
Attesting Officer    *Director of the United States Patent and Trademark Office*